United States Patent
Dascalu

(12) 
(10) Patent No.: US 11,298,072 B2
(45) Date of Patent: Apr. 12, 2022

(54) DERMOSCOPY DIAGNOSIS OF CANCEROUS LESIONS UTILIZING DUAL DEEP LEARNING ALGORITHMS VIA VISUAL AND AUDIO (SONIFICATION) OUTPUTS

(71) Applicant: Avi Dascalu, Tel-Aviv (IL)

(72) Inventor: Avi Dascalu, Tel-Aviv (IL)

(73) Assignee: BOSTEL TECHNOLOGIES, LLC, Rockland, MA (US)

( * ) Notice: Subject to any disclaimer, the term of this patent is extended or adjusted under 35 U.S.C. 154(b) by 93 days.

(21) Appl. No.: 16/445,684

(22) Filed: Jun. 19, 2019

(65) Prior Publication Data

US 2019/0336063 A1 Nov. 7, 2019

Related U.S. Application Data

(63) Continuation-in-part of application No. 16/311,372, filed as application No. PCT/US2017/039189 on Jun. 26, 2017.

(Continued)

(51) Int. Cl.
*A61B 5/00* (2006.01)
*G06N 3/02* (2006.01)
(Continued)

(52) U.S. Cl.
CPC .......... *A61B 5/444* (2013.01); *A61B 5/0064* (2013.01); *A61B 5/7267* (2013.01); *G06N 3/02* (2013.01); *A61B 5/0077* (2013.01); *A61B 5/445* (2013.01); *A61B 5/7257* (2013.01); *G06F 40/58* (2020.01); *G06N 20/00* (2019.01); *G06T 7/0012* (2013.01);
(Continued)

(58) Field of Classification Search
CPC ..... A61B 5/444; A61B 5/0064; A61B 5/7267; G06N 3/02
See application file for complete search history.

(56) References Cited

U.S. PATENT DOCUMENTS 6,215,893 B1 4/2001 Leshem et al.
7,510,398 B1 * 3/2009 Thornton ............. G09B 23/288
434/262

(Continued)

FOREIGN PATENT DOCUMENTS

WO WO2006114003 11/2006
WO WO2011087807 A2 7/2011

OTHER PUBLICATIONS

Ahmad, Adeel et al. Sonification of optical coherence tomography data and images. *Opt Express*. May 10, 2010; 18(10): 9934-44.

(Continued)

*Primary Examiner* — Qun Shen
(74) *Attorney, Agent, or Firm* — Casimir Jones, S.C.; Tristan A. Fuierer; Marianne Fuierer

(57) ABSTRACT

The present invention provides for a system and method for the diagnosis of skin cancer, wherein visual data is acquired from a skin lesion by a passive or active optical, electronical, thermal or mechanical method, processing the acquired visual field image into a classifier, applying a dermoscopic classification analysis to the image and converting, by sonification techniques, the data to raw audio signals, wherein the raw audio signals are analyzed with a second machine learning algorithm to increase interpretability and the precision of diagnosis.

18 Claims, 8 Drawing Sheets

Visual representations of sonification audio files.

Raw WAV files (amplitude) from sonification, benign lesion examples

Raw WAV file (amplitude) from sonification, malignant lesion examples

Related U.S. Application Data

(60) Provisional application No. 62/765,042, filed on Aug. 17, 2018, provisional application No. 62/688,062, filed on Jun. 21, 2018, provisional application No. 62/357,394, filed on Jul. 1, 2016.

(51) Int. Cl.
  *G06T 7/00* (2017.01)
  *G06N 20/00* (2019.01)
  *G06F 40/58* (2020.01)

(52) U.S. Cl.
  CPC ............. *G06T 2207/30088* (2013.01); *G06T 2207/30096* (2013.01)

(56) References Cited

U.S. PATENT DOCUMENTS

| | | | |
|---|---|---|---|
| 10,328,276 B2* | 6/2019 | Williams | A61N 5/06 |
| 2004/0077950 A1 | 4/2004 | Marshik-Geurts et al. | |
| 2005/0248474 A1 | 11/2005 | Wiser et al. | |
| 2006/0120608 A1 | 6/2006 | Luo et al. | |
| 2006/0269111 A1 | 11/2006 | Stoecker et al. | |
| 2008/0013747 A1* | 1/2008 | Tran | A61B 7/04 381/67 |
| 2009/0316970 A1 | 12/2009 | Kemper et al. | |
| 2010/0111392 A1 | 5/2010 | Valadez et al. | |
| 2012/0008838 A1* | 1/2012 | Guyon | G06T 7/62 382/128 |
| 2012/0136255 A1 | 5/2012 | Fan et al. | |
| 2012/0185418 A1* | 7/2012 | Capman | G06F 3/165 706/12 |
| 2013/0102877 A1 | 4/2013 | Mori et al. | |
| 2014/0036054 A1* | 2/2014 | Zouridakis | A61B 5/0077 348/77 |
| 2015/0055855 A1 | 2/2015 | Rodriguez et al. | |
| 2016/0322066 A1* | 11/2016 | Sharifi | G06F 16/683 |
| 2017/0132526 A1* | 5/2017 | Cohen | G06N 5/022 |
| 2017/0262433 A1* | 9/2017 | Chester | G06F 40/45 |
| 2017/0262479 A1* | 9/2017 | Chester | G06F 16/583 |
| 2017/0286979 A1* | 10/2017 | Chavez | G06Q 20/04 |
| 2019/0053760 A1 | 2/2019 | Gerald et al. | |
| 2019/0102878 A1 | 4/2019 | Zhang et al. | |

OTHER PUBLICATIONS

AHRQ Publication No. 11-EHC085-EF, Noninvasive Diagnostic Techniques for the Detection of Skin Cancers, Sep. 2011.

American Cancer Society. Cancer facts & figures 2016. Atlanta, American Cancer Society 2018. http://www.cancer.org/acs/groups/content/@research/documents/document/acspc-047079.pdf. https://www.cancer.org/research/cancer-facts-statistics/all-cancer-facts-figures/cancer-facts-figures-2018.html.

Bejnordi, Babak, E. et al. Diagnostic Assessment of Deep Learning Algorithms for Detection of Lymph Node Metastases in Women With Breast Cancer. *JAMA*. 2017; 318(22):2199-2210.

Brunssen, A. et al. Impact of skin cancer screening and secondary prevention campaigns on skin cancer incidence and mortality: A systematic review. *J Am Acad Dermatol*. 2017, 76(1):129-139.

Carrera, C. et al. Validity and Reliability of Dermoscopic Criteria Used to Differentiate Nevi From Melanoma: A Web-Based International Dermoscopy Society Study. *JAMA Dermatol*. 2016, 152(7):798-806.

Dubus, G. et al. A systematic review of mapping strategies for the sonification of physical quantities. *RPLoS One*. 2013, 17;8(12) e82491.

Elmore, J.G. et al. Pathologists' diagnosis of invasive melanoma and melanocytic proliferations: observer accuracy and reproducibility study. *BMJ*. 2017, 357: j2813|doi:10.1136/bmj.j2813.

Esteva, A. et al. Dermatologist-level classification of skin cancer with deep neural networks. *Nature*. 2017, 542(7639):115-118.

Gaizauskas, Barbara R. The Harmony of the Spheres. *Journal of the Royal Astronomical Society of Canada*, 1974, 68:146-151.

Gendreau, J.L. et al. Unimaged Melanomas in Store-and-Forward Teledermatology. *Telemed J E Health*. 2017, 23(6):517-520.

Gulshan, V. et al. Development and Validation of a Deep Learning Algorithm for Detection of Diabetic Retinopathy in Retinal Fundus Photographs. *JAMA*. 2016, 316(22):2402-2410.

Han, Y.C. et al. Skin Pattern Sonification as a New Timbral Expression. *Leonardo Music Journal*, vol. 24, 2014, pp. 41-43.

Han, S.S. et al. Classification of the Clinical Images for Benign and Malignant Cutaneous Tumors Using a Deep Learning Algorithm. *J Invest Dermatol*. 2018, pii: S0022-202X (18)30111-8.

Ioffe, Sergey et al. Batch Normalization: Accelerating Deep Network Training by Reducing Internal Covariate Shift. In Proceedings of the 32nd International Conference on Machine Learning (ICML), 2015 (vol. 37). Lille, France.

King, Andrew J. Multisensory Integration: Strategies for Synchronization. *Current Biology*, 2005, 15(9):R339-R341.

Li, X. et al. Deep Saliency: Multi-Task Deep Neural Network Model for Salient Object Detection. *IEEE Trans Image Process*. 2016, 25(8):3919-30.

Matsumoto, M. et al. Estimating the cost of skin cancer detection by dermatology providers in a large health care system. *J Am Acad Dermatol*. 2018, 78(4):701-709.e1.

Melamed, R.D. et al. Genomic Characterization of Dysplastic Nevi Unveils Implications for Diagnosis of Melanoma. *J Invest Dermatol*. 2017;137(4):905.

Neuhoff, J.G. et al. Pitch and loudness interact in auditory displays: can the data get lost in the map. *J Exp Psychol Appl*. 2002, 8(1):17-25.

Poveda, Jonatan et al. Portable neonatal EEG monitoring and sonification on an Android device. *Conf Proc IEEE Eng Med Biol Soc*. Jul. 2017; 2017:2018-2021.

Russakovsky, O. et al. ImageNet Large Scale Visual Recognition Challenge. *International Journal of Computer Vision*, 2015, 115(3), 211-252.

Scholz, Daniel S. et al. Sonification as a possible stroke rehabilitation strategy. *Front Neurosci*. 2014, 8(332)1-7.

Shraddha, Shukla et al. A Review on K-means data Clustering approach. *International Journal of Information & Computation Technology*. ISSN 0974-2239 vol. 4, No. 17 (2014):1847-1860.

Tschandl, P. et al. Melanomas vs. nevi in high-risk patients under long-term monitoring with digital dermatoscopy: do melanomas and nevi already differ at baseline? *JEurAcad Dermatol Venereol*. Jun. 2017;31(6):972-977.

Waldmann, A. et al. Frequency of excisions and yields of malignant skin tumors in a population-based screening intervention of 360,288 whole-body examinations. *Arch Dermatol*. 2012;148(8):903-910.

Walker, Bruce N. et al. Theory of Sonification. In T. Hermann, A. Hunt, & J. Neuhof (Eds.), *The Sonification Handbook* (pp. 9-39). Berlin, Germany: Logos Publishing House, 2011, ISBN 978-3-8325-2819-5.

Winkelmann, R.R. et al. Integrating Skin Cancer-Related Technologies into Clinical Practice. *Dermatol Clin*. Oct. 2017;35(4):565-576.

Yu, Lequan, et al. Automated Melanoma Recognition in Dermoscopy Images via Very Deep Residual Networks. *IEEE Trans Med Imaging*. Apr. 2017; 36(4): 994-1004.

Zortea, M. et al. Automatic learning of spatial patterns for diagnosis of skin lesions, 32$^{nd}$ Annual International Conference of the IEEE EMBS, Buenos Aires, Argentina, Aug. 31-Sep. 4, 2010.

Extended European Search Report, corresponding to European Patent Application No. 17820991.2, dated Mar. 6, 2020.

Annes Si, G. et al. Sensitivity, specificity, and diagnostic accuracy of three dermoscopic algorithmic methods in the diagnosis of doubtful melanocytic lesions: the importance of light brown structureless areas in differentiating atypical melanocytic nevi from thin melanomas. *J Am Acad Dermatol*. (May 2007); 56(5): 759-67.

Campos-do-Carmo, G. et al. Dermoscopy: basic concepts. *Int J Dermatol*. (Jul. 2008) ; 47(7): 712-9.

Eggermont, A.M. et al. Cutaneous melanoma. *Lancet*. (Mar. 1, 2014); 383(9919): 816-27.

(56) References Cited

OTHER PUBLICATIONS

Ferris, L.K. et al. New diagnostic aids for melanoma. *Dermatol Clin.* (Jul. 2012); 30(3): 535-545.

Mayer, J.E. et al. Screening, early detection, education, and trends for melanoma: Current status (2007-2013) and future directions: Part I. Epidemiology, high-risk groups, clinical strategies, and diagnostic technology. *Journal of the American Academy of Dermatology*, (Oct. 2014) 71:4: 599. e1-e12.

Noor, O. et al. A dermoscopy survey to assess who is using it and why it is or is not being used. *Int J Dermatol.* (Sep. 2009); 48(9): 951-2.

Russo, T. et al. Dermoscopy of Malignant Skin Tumours: What's New? *Dermatology* (2017) 233-:64-73.

Siegel, R. et al. Cancer statistics, 2012. CA *Cancer J Clin.* (Jan.-Feb. 2012); 62(1): 10-29.

Tsao, H. et al. Early detection of melanoma: reviewing the ABCDEs. American Academy of Dermatology Ad Hoc Task Force for the ABCDEs of Melanoma, *J Am Acad Dermatol.* (Apr. 2015.) 72(4): 717-23.

\* cited by examiner

Visual representations of sonification audio files.

Fig. 1a  Raw WAV files (amplitude) from sonification, benign lesion examples

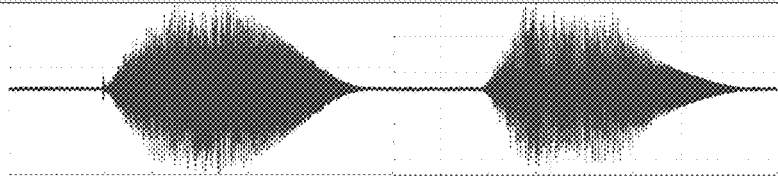

Fig. 1b  Raw WAV file (amplitude) from sonification, malignant lesion examples

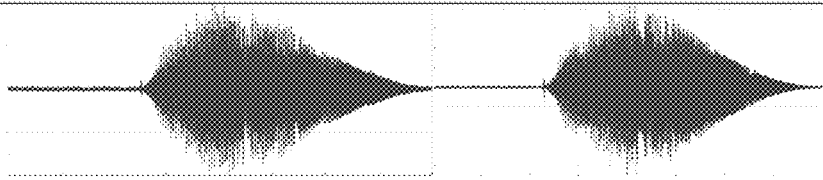

Fig. 1c  FFT of sonification output, benign lesion examples

Fig. 1d  FFT of sonification output, malignant lesion examples

Fig. 1e  Spectrogram of sonification output, benign lesion examples

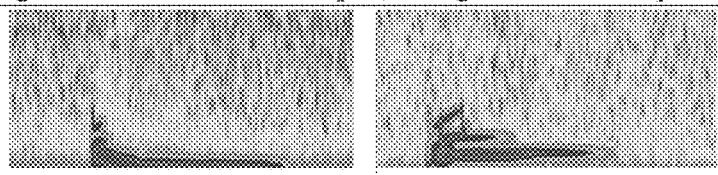

Fig. 1f  Spectrogram of sonification output, malignant lesion examples

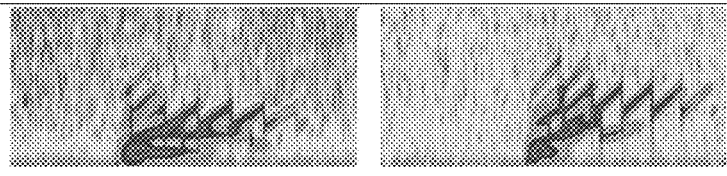

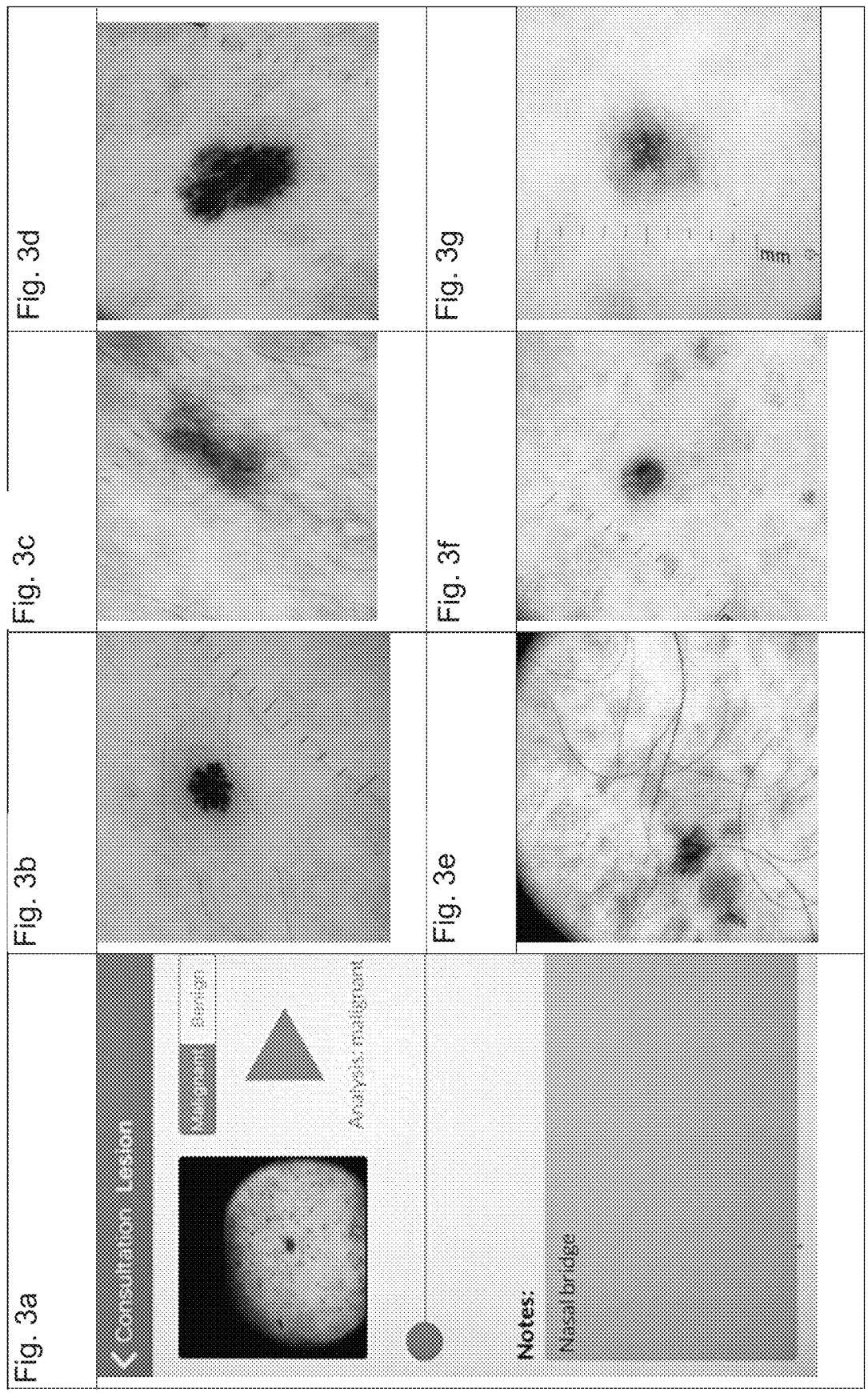

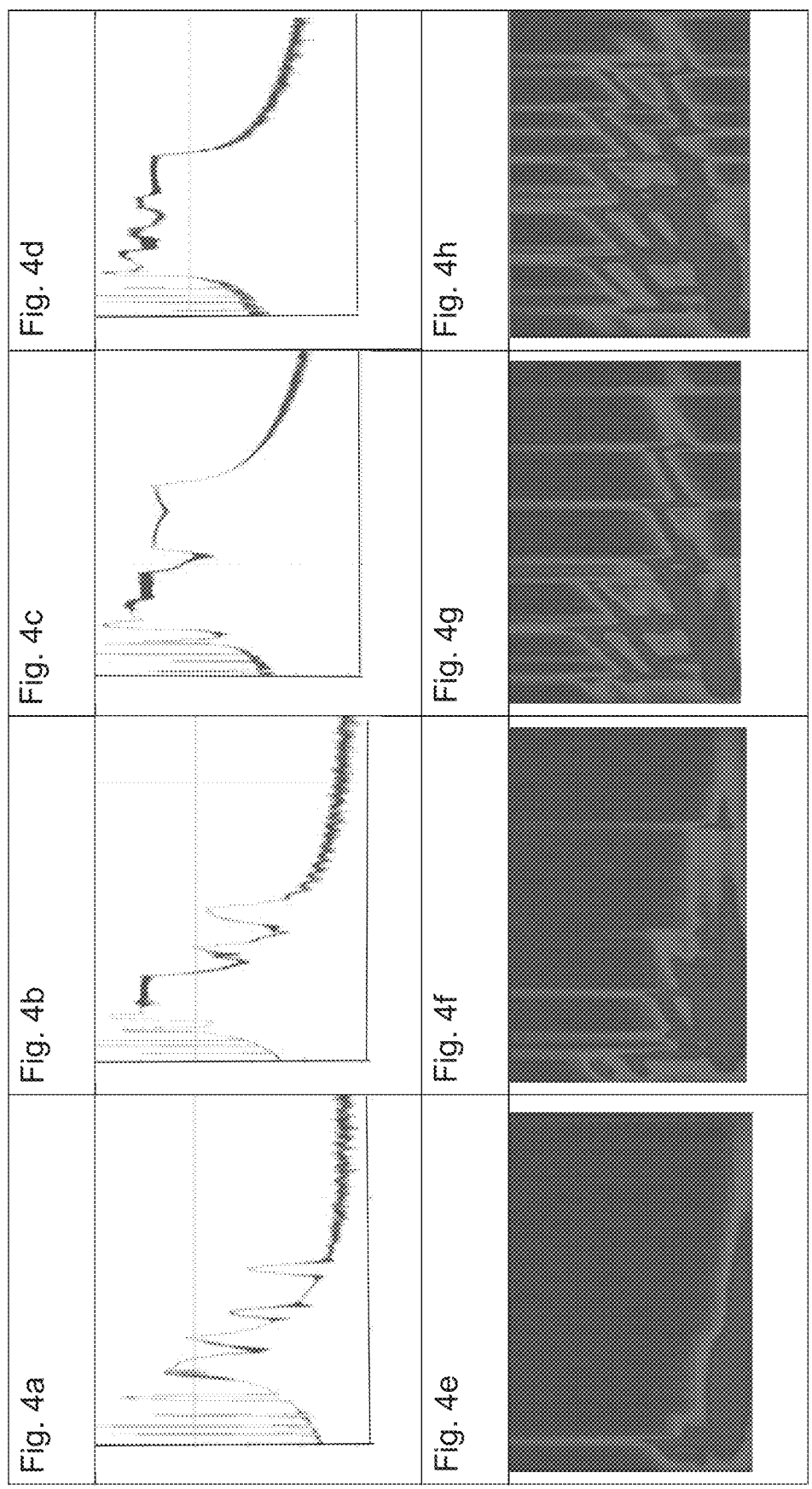

Summary of Classification Performances in Clinical Trial

Fig. 5A

Classifier Data

| | Malignant Lesions | |
|---|---|---|
| True positive | | 13 |
| False negative | | 11 |
| | Benign Lesions | |
| False positive | | 1 |
| True negative | | 22 |

| Output: | |
|---|---|
| Sensitivity | 54.17% |
| Specificity | 95.65% |
| Positive predictive value | 92.86% |
| Negative predictive value | 66.67% |

Fig. 5B

Sonification Kmeans

| | Malignant Lesions | |
|---|---|---|
| True positive | | 22 |
| False negative | | 2 |
| | Benign Lesions | |
| False positive | | 7 |
| True negative | | 16 |

| Output: | |
|---|---|
| Sensitivity | 91.67% |
| Specificity | 69.57% |
| Positive predictive | 75.86% |
| Negative predictive | 88.89% |

Fig. 5C

Combined Clinical Diagnosis

| | Malignant Lesions | |
|---|---|---|
| True positive | | 22 |
| False negative | | 2 |
| | Benign Lesions | |
| False positive | | 1 |
| True negative | | 22 |

| Output: | |
|---|---|
| Sensitivity | 91.67% |
| Specificity | 95.65% |
| Positive predictive | 95.65% |
| Negative predictive | 91.67% |

DERMOSCOPY DIAGNOSIS OF CANCEROUS LESIONS UTILIZING DUAL DEEP LEARNING ALGORITHMS VIA VISUAL AND AUDIO (SONIFICATION) OUTPUTS

CROSS REFERENCE TO RELATED APPLICATIONS

This application is a Continuation-in-Part application claiming priority to copending U.S. patent application Ser. No. 16/311,372 which was filed under the provisions of 35 U.S.C. § 371 and claims the priority of International Patent Application No. PCT/US2017/039189 filed on Jun. 26, 2017 which in turn claims priority to U.S. Provisional Patent Application No. 62/357,394 filed on Jul. 1, 2016, and further claims priority to U.S. Provisional Application No. 62/688,062 filed on Jun. 21, 2018 and U.S. Provisional Application No. 62/765,042 filed on Aug. 17, 2018, the contents of which are hereby incorporated by reference herein for all purposes.

BACKGROUND OF THE INVENTION

Field of the Invention

The present invention provides for a system and method for the diagnosis of skin cancer. Pre-cancerous and/or other atypical skin lesions, including atypical moles, more specifically for a system and method for acquiring visual data from a skin lesion by a passive or active optical, electronical, thermal or mechanical method, processing the acquired visual field image into a classifier, applying a dermoscopic classification analysis to the image and converting, by sonification techniques, the data to audio signals, analyzing the audio signal with an additional sonification-derived diagnostic layer using a second machine learning algorithm to analyzed the raw sound files to increase interpretability and the precision of diagnosis.

Related Art

Malignant melanoma (MM) is a cancer claiming about 90,000 new cases per year in the US alone.[1] The gold standard for diagnosis of skin cancer is dermoscopy[2] which results in a limited diagnostic accuracy due to the complexity of visual inputs embedded in a dermoscopy image, and its dependency on physician skills. For example, dermatologists achieve a mean sensitivity for MM detection of 40%[3] and for more complex melanoma images detection is not better than chance. The number of biopsies that need to be excised in order to identify one melanoma at ages <50 is 58:1,[4] and 28:1 at all ages.[5]

Additional monitoring techniques are experimental and unavailable to most dermatologists and primary care providers.[6] National skin cancer screening programs are beneficial only at a very low evidence level,[7] rendering accurate MM diagnosis an imperative social and economical task.

A Deep Learning (DL) classifier can be utilized in order to interpret complex visual data through image feature extraction and pattern analysis, such as to diagnose diabetic retinopathy of retinal fundus[8] and detection of lymph node metastases in women with breast cancer.[9] In dermatology applications, DL classifiers can achieve a diagnostic performance equal or superior to dermatologists' accuracy.[10,11] However, it was found in the International Patent Application No. PCT/US2017/039189 that the use of sonification of the output data from DL classifiers greatly increased accuracy. The present invention provides a further improvement for the identification of cancerous tissue.

SUMMARY OF THE INVENTION

The present invention provides a method to distinguish between cancerous and/or other pre-cancerous atypical tissue and non-cancerous tissue, specifically the difference between melanoma and non-melanoma type tissue. The present invention provides for a system and method for diagnosing skin cancer that provides for a more effective analysis of changes in skin tissue due to the duality of acquiring visual data and transforming such visual data into an audio signal wherein deep learning algorithms are used in both analyzing the visual data and audio signals to enhance precision of the diagnosis.

In one aspect, the present invention provides for a method of diagnosing skin cancer, the method comprising:
  providing a tissue image of a tissue sample suspected of being cancerous, wherein the tissue image is created by photography, dermoscopy, electricity, molecular scattering or thermography;
  generating a plurality of pixel segmentation of the tissue image, wherein each pixel segmentation is classified as specific type of tissue;
  classifying each type of tissue by an associated Classifier to provide a plurality of classifier features based on shape, content and color;
  introducing the plurality of classifier features into a Clustering algorithm to provide for centroids of data relating to the classifier features;
  applying a raw audio signal for each of the centroids of data; and
  introducing the raw audio signal for each of the centroids of data into an additional machine learning algorithm thereby providing for a visual and/or audio output for diagnosing the tissue sample suspected of being cancerous.

Notably, the data from the clustering algorithm or additional machine learning algorithm can be visualized by grouping observations by K-means, hierarchical clustering or feature agglomeration.

In yet another aspect, the present invention provides for a method of analyzing a tissue sample for determining suspected cancerous tissue, the method comprising:
  a. providing a tissue image of the sample tissue;
  b. transmitting the tissue image to a computer aided classification system;
  c. extracting features from the tissue image with the computer aided classification system for classifying the tissue image, wherein extracted features characterize the sample tissue and such sample characterization is compared to characterization of a reference tissue to classify and provide classified features of the sample tissue;
  d. applying an unsupervised or semisupervised clustering process to the classified features to provide a plurality of clusters;
  e. applying a specific audio signal for each of the plurality of clusters; and
  f. introducing the specific audio signal for each of the plurality of clusters into an additional machine learning algorithm thereby providing for a visual and/or audio output to provide enhanced identification of the tissue sample.

In a still further aspect, the present invention a method for analysis and diagnosis of the presence of cancerous tissue, the method comprising:
a. applying electromagnetic or mechanical energy to skin tissue suspected of being malignant;
b. capturing reflected and/or refracted electromagnetic or mechanical energy through a dermoscope or microscope;
c. converting the reflected and/or refracted or acquired energy into a visual image;
d. transmitting the input image to a classifier database;
e. generating a feature map by applying a deep learning classifier to the input image;
f. assigning dermoscopic patterns to the feature map generated by the classifier,
g. converting the dermoscopic patterns into an audio signal by use of a clustering algorithm selected from a supervised, unsupervised, semisupervised, reinforcement learning or combination thereof;
h. generating a raw audio signal from the output of the clustering algorithm; and
i. applying a second deep learning classifier to the raw audio signal, wherein the output reflects the differences shown in the dermoscopic pattern to provide guidance for excising skin tissue suspected of being malignant.

In the present invention, the deep learning techniques may include the use of either of or a combination of supervised, unsupervised, semisupervised or reinforcement learning including a convolutional neuronal network, for example, and combining data analysis by use of a known inception analysis architecture for computer vision, such as Inception v Networks (1, 2, 3 or 4). The deep learning algorithm generates an audio signal which comprises different output sounds differentiated by frequency, duration, magnitude, spectrum, and spatial orientation and reflecting the differences shown in the dermoscopic pattern, as identified by their musical parallel of pitch, rhythm, tempo, dynamics and timbre which can further be analyzed by a second deep learning algorithm providing an decisive output for excise or non-excise guidance.

Importantly, the conversion of the dermoscopic pattern into an audio signal is preferably accomplished by a parameter mapping sonification method wherein a classification method and/or clustering algorithm is used to isolates clusters of data related to each tissue type and then assigned a unique sound to each tissue type. Such classification method may include but is not limited to raw weights classification, concept mapping classification and K-Means cluster analysis.

In a further aspect, the present invention provides for a non-invasive phonodermoscopy system for testing of skin tissue to determine cancerous effects, the system comprising:
a. a device for obtaining visual data of the skin tissue, wherein electromagnetic energy in infrared, visual and ultraviolet spectrum are applied to the skin tissue and refracted and/or reflected electromagnetic energy is captured to provide the visual data;
b. an audio device to provide a specific audio signal output for each cluster in the output cluster set; and
c. a processor operatively responsive to capture both the visual data and audio signal output, wherein a least one computer aided deep learning algorithm to provide different patterns of audio intensity and/or visual contrasts of tissue to provide an output cluster set defining the skin tissue.

In yet another aspect, the present invention provides for a system to diagnose cancer of a skin lesion, the system comprising:
a. a unit for capturing electromagnetic waves from the skin lesion;
b. a direct input raw digital data visual screen communicatively connected to the unit for receiving captured electromagnetic waves from the skin lesion;
c. a visual data processing unit for converting the electromagnetic waves to a visual image;
d. a computer processor for processing classifier data and converting the visual image into classified data;
e. a dermoscopic pattern transduction analysis unit using a clustering program to convert classified data into a multiplicity of clusters;
f. a visual to audio transducer for converting the multiplicity of clusters into raw audio signals;
g. a computer processor for processing the raw audio signals and converting into refined output comprising an audio signal and/or visual graph; and
a media device for capturing and sharing a diagnostic output including but not limited to a computer, tablet, mobile device, phone, watch, ear-worn device such as headphones, Bluetooth device or a device that provides a tactile or vibration signal, to provide an audio/visual/tactile output to a subject. The term "computing processor" may be used interchangeably with "client device", "mobile device", "computing system", "computer system", "server", "networked device", "networked computing device", "networked computer system", and "networked computing system".

In another aspect, the present invention provides for a method for examining an atypical skin lesion to determine whether to excise or not to excise the atypical skin lesion, the method comprising:
providing a tissue image of the atypical skin lesion;
generating segmentation of the tissue image, wherein similar types of tissue or features are grouped into one segment to provide a plurality of different segments comprising different types of tissue or features;
classifying each of the plurality of segments to provide a plurality of classified segments;
applying a clustering process to the classified segments to provide a plurality of clusters;
applying a specific audio signal for each of the plurality of clusters to provide a raw audio output; and
introducing the raw audio output to an additional deep learning algorithm for providing an enhanced audio or visual signal to indicate if the atypical skin lesion is either malignant or non-malignant tissue thereby providing guidance to excise or not to excise the atypical skin lesion.

An atypical skin lesion includes lesions that are growing, spreading or pigmented, and/or those that occur on exposed areas of skin are of particular concern. Such lesions may include but is not limited to atypical melanocytic hyperplasia, atypical mole, dysplastic mole, cancerous skin diseases, actinic keratosis, basal and squamous cell carcinoma, etc.

To an artisan skilled in the art, sonification is a means of transforming and interpreting visual data, i.e. turning acquired image pixels into sound. Images to be transformed into the language of sonification and turned into sound files are exemplified but not limited to dermoscopy, radiology, MRI, CT, pathology, eye fundus, otoscopy, gastroscopy, colonoscopy, bone density scan, breast ultrasound, drug design.

In another aspect, the present invention can be used in genomic drug targeting, drug target discovery and targeted drug networks. For example, the data processing and sonification of such data processing results either as an audio signal or further processed through a machine learning algorithm, as described in the present invention, can be used for analysis of data from medical databases to be used for discovering biological elements (e.g. genes, proteins, biomarkers, biomolecules, biological pathways, biological functions, environmental factors, nutritional factors, etc.) that are associated with diseases and medical syndromes. Specifically, the present invention employs preprocessing and frequency analysis on raw medical data with data mining algorithms thereby extracting knowledge needed to associate diseases and medical syndromes with particular biological elements and environmental and nutritional factors. In addition, it also identifies direct and indirect associations between medical topics using Clustering Algorithms. The results from each data mining algorithm provide different insights and knowledge aspects of the transformed data that can be combined into a final result.

Other features and advantages of the invention will be apparent from the following detailed description and claims.

BRIEF DESCRIPTION OF THE FIGURES

FIGS. 1 a, b, and c shows the visual representations of sonification audio files, FIGS. 1 a and b show Raw WAV files (amplitude) from sonification, FIGS. 1 c and d show FFT of sonification output and FIGS. 1 e and f show Spectrogram of sonification output.

FIGS. 3 a, b, c, d, e, f and g shows Clinical Trial Example Images, FIG. 3a depicts the smartphone application of a malignant lesion, FIGS. 3 b to f and of those not recognized by System B, as shown in FIG. 3g are representative clinical examples of the dysplastic nevi excised which were identified.

FIGS. 4 a, b display a low y-axis span and do not display a >3000 Hz frequency, contrary to malignant dermoscopies of FIGS. 4 c, d; Spectrograms of benign FIGS. 4 e, f and malignant skin lesions FIGS. 4 g, h, FIG. 4i compares benign and malignant lesions.

FIGS. 5 A, B, C shows a summary of the performance results of System A (DL classifier), shown in FIG. 5 A, FIG. 5 B shows System B (sonification and LARS-based heuristic inspection), as well as the combined System A+B in the clinical trial, as shown in FIG. 5 C.

DETAILED DESCRIPTION OF THE INVENTION

The present invention uses a deep learning (DL) classifier that is trained to visually analyze dermoscopy images, in order to identify cancerous lesions, pigmented (MM, dysplastic nevi) or skin carcinomas. Classification of a lesion is dichotomous, as malignant or benign, and enables a clinical decision support system indicating the requirement for a biopsy. This single-stage DL system is an effective MM diagnostic aid, on its own. However, in the present invention the diagnostic accuracy is further boosted by an analysis technology in which output from the DL classifier is systematically converted into sound ("sonification"[12]), and then the sound file is analyzed by a second DL classifier to indicate a malignant or benign lesion.

Figure 6:
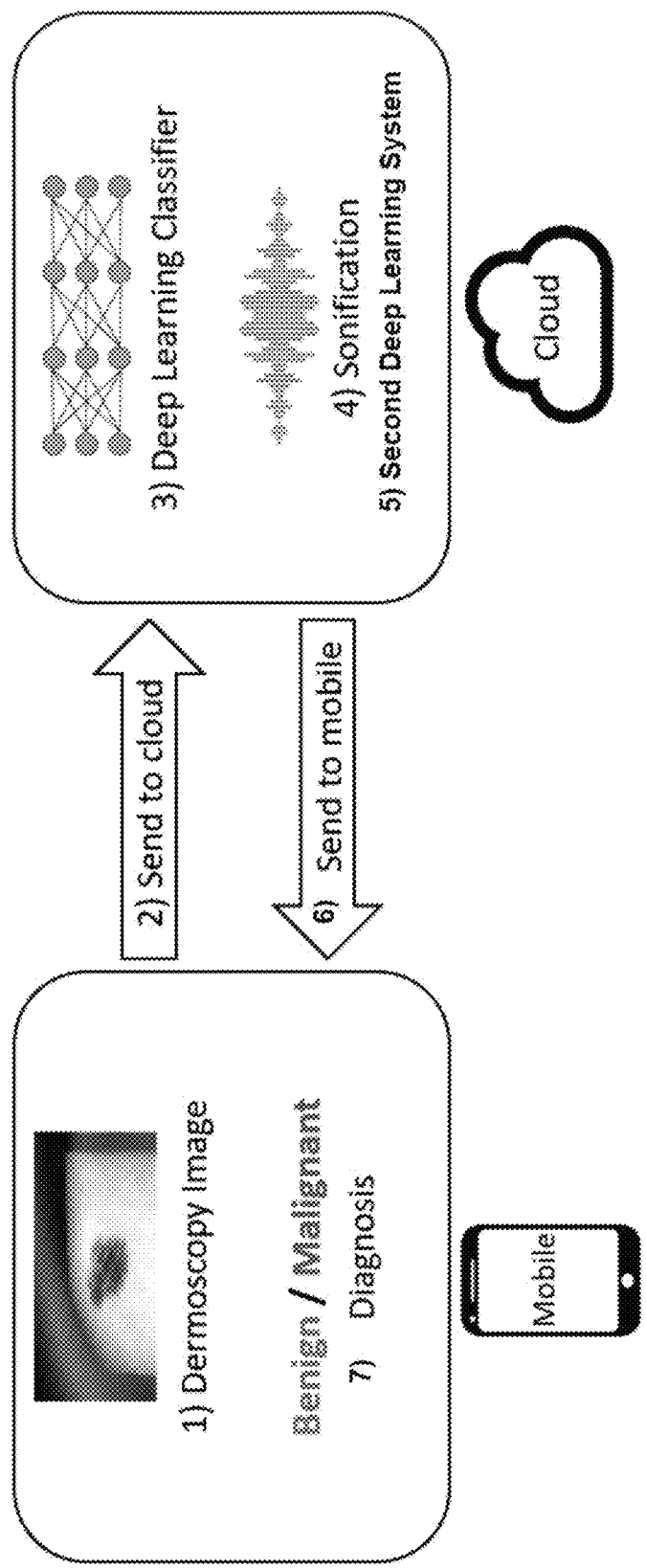
FIG. 6 shows a flowchart of present image processing. A dermoscopy image is acquired by a smartphone and conveyed to cloud computing. A deep learning classifier predicts primary findings which are further processed by sonification and results are analyzed by a second learning system. Final diagnosis is conferred to user as a malign or benign lesion diagnosis, i.e. excise or not indication.
Figure 7:
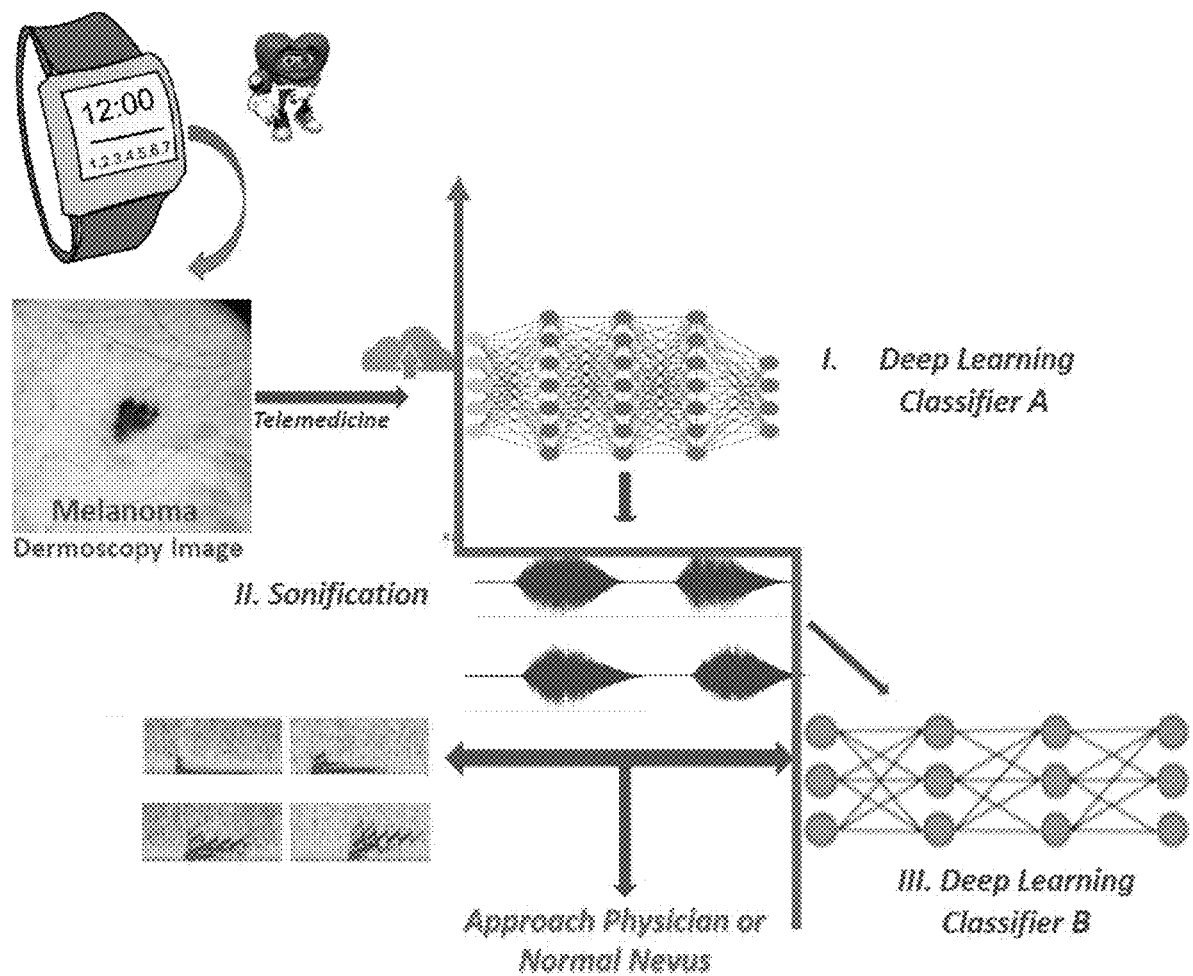
FIG. 7 shows a watch or peripheral apparatus for imaging and diagnosing nevi and skin maladies

The present invention further includes the capture of lesion images by a dermoscope attached to a mobile phone and submitted via a purpose-built secure app to the classifier operating in the cloud. Instantaneous diagnosis is returned to bedside after the machine learning analysis from the image and subsequent sonic output analyzed by a second machine learning system as shown in FIG. 6. Further, FIG. 7 shows a watch or peripheral apparatus, for example a blood pressure monitor, that is employed in order to acquire by camera both an image and/or dermoscopic lens of a skin lesion. Image is transmitted to server and undergoes a Deep Learning, Sonification procedure and second Deep Learning in order to derive a diagnosis, which is returned to patient either as Normal or the need to approach a physician.

The present invention provides for a medical device system and method for diagnosing skin lesions, or skin cancers, and particularly, skin tumors of melanocytic origin, i.e. malignant melanoma or non-melanocytic skin tumors, such as basal and squamous cell carcinoma. The present invention relates to a device which (i) acquires visual data from a skin lesion by an optical or mechanical method, or captures visual data by a sensor refracted electromagnetic waves such as UVA, visible spectrum or infrared wavelengths or molecular vibrations, (ii) processing visual data to provide a visual field image; (iii) applies a dermoscopic pattern analysis to the acquired visual image and (iv) transforms the data into an audio signal, assigning different audio pitch, loudness, timbre, spatialization and temporal patterns of sound to each visual pattern, to be further subjected to a second algorithm for increasing the accuracy to the practitioner.

An audio signal is important for further identification of the suspected cancerous tissue. Notably, the Calyx of Held, first described in 1893, is a giant glutamate secreting relay synapse in the auditory mammalian brainstem. It is involved in transduction of sound into neuronal activity and relatively fast transmission of auditory input. Upon stimulation, sound waves transduction follows a mechanical process, lasting for about 1 ms, contrary to processing of visual stimuli, a photochemical operation lasting for about 50 ms. Due to this at least 50 fold factor slower processing of visual input, auditory input can be quickly perceived and delivered to consciousness. Part of this delay for visual stimuli may be related to longer and slower neuronal pathways of delivering information to the cortex.[23]

Thus, the sensitivity of the acoustic systems overcomes the vision system. If the audio and visual input are close to the perceiver, no brain compensation and adjustment of brain function are applied to, rendering a higher resolution rate and more stimuli identification for the acoustic signal than the visual function.

Data transformation into acoustic parameters which represent the acquired information, i.e. sonification, was used from the ancient Greek period and Medieval China to provide information of elapsed time. In the middle ages it was used by Kepler, finally contributing to his third law of planetary motion.[24] Sonification in various adaptations was used or proposed to be used, amongst others, as a highly perceptive substitute to visual information as apparatus providing warnings to pilots, device for monitoring architectural integrity of large structures, guiding the manipulation of surgical instruments during brain surgery, anesthesiology, analyzing seismology data, data display for the visually impaired, monitoring the oscillation of subatomic particles in quantum physics, fingerprint identification, skin pore audification by area and color distribution, training and rehabilitation, seizure detection in infants, optical coherence tomography monitoring, stroke rehabilitation.[25, 26, 27, 28, 29]

As previously stated, cancers of the skin are the most common forms of cancer. There are several modalities[30], discussed hereinbelow, to assist with generating visual data and/or images for further sonification of data.

Photography is a technique that uses photographic devices to capture surface images of the skin in order to primarily identify suspicious and pigmented skin lesions. Polarized light photography relies on the fact that reflected light has two components, one regular reflectance to reflect the skin surface morphology, the other "back-scattered" from within the tissue. It is useful in the assessment of skin surface morphology when the proper polarizing filters and techniques are used.

Dermoscopy, also known as epiluminescence microscopy, uses handheld devices to show subsurface structures of the skin and optical light ray penetration beyond the skin surface and minimize surface reflection. Different types of dermoscopy include nonpolarized light contact dermoscopy that uses a nonpolarized light source such as a halogen light source and requires the use of an oil or gel to prevent surface reflection, attached directly to the skin mechanically. Additionally, dermoscopy can include the use of non-polarized dermoscopy devices that do not need a liquid interface and are equipped with a cross-polarized lens that absorbs scattered light waves. Polarized contact dermoscopy can attain the images of vascular and other structures. These devices are useful in visualizing melanin, blue nevi, and shiny white streaks. Still further, both devices can be combined.

Thermography involves the measuring and mapping surface skin temperature through direct contact (via application of liquid crystal plates to a part of the body) or at a distance (utilizing a highly-sensitive medical infrared camera and sophisticated computer interface). Thermography can be used in conjunction with thermostimulation which applies thermal stress on the skin to be examined.

Other methods of providing an image include the use of multiphoton fluorescence microscopy or multiphoton excitation microscopy to illuminate endogenous fluorophores in skin tissues, which emits a fluorescence signal to be captured by a detector. Additionally, optical coherence tomography (OCT) may be used and this device utilizes reflected light to produce cross-sectional subcutaneous images of tissue at a resolution equivalent to a low-power microscope. Confocal scanning laser microscopy (CSLM) works by first projecting a low-power laser beam through a lens on a specific point on the skin, and then detecting the light reflected from the focal point through a confocal pinhole filter. The reflected light is transformed into an electrical signal, which is recorded as an image by a computer.

Photodynamic diagnosis includes the use of topical agents that stimulate the production of endogenous photosensitizers that produce a photodynamic effect when exposed to light of certain wavelengths and energy. For example, UV is absorbed by melanin. The theory behind this experimental technique is that illumination by ultraviolet light could reveal irregular pigment distribution, and therefore could be useful in defining the borders of melanoma.

The features extracted from the image are then used to classify the image wherein the classification step is comprised of characterizing the tissue based on features such as shape, color, size, or quality of the tissue, to name a few, and the characterization of a tissue is compared to the characterization of a reference tissue and the tissue is classified based on the comparison.

Embodiments of present invention employ computer aided classification systems (sometimes termed "machine learning," or "deep learning"). There is a plethora of pattern recognition algorithms to employ to biometrically model and classify different tissue types. Those skilled in the art will recognize that many such classifications systems could be used in the present invention, including but not limited to Linear Discriminant Analysis (LDA), Kernel Discriminant Analysis (KDA), Neighborhood Preserving Embedding (NPE), Orthogonal Linear Graph Embedding (OLGE), Unsupervised Discriminant Projection (UDP), Marginal Fisher Analysis (MFA), Locality Preserving Projection (LPP), Local Fisher Discriminant Analysis (LFDA), Convolutional Neural Network (CNN), Support Vector Machine (SVD) and Kernel Correlation Feature Analysis (KCFA).

A preferred classification system is the CNN system that is used in order to automatically extract local feature. Some examples of a CNN system include Lenets, Alexnet, Overfeat, VGG, RESNET, Googlenet and Inception (V2, V3, V4), ENET and Xception. CNN consists of many layers, each layer plays a feature extraction role and performs different operators such as convolutions, subsampling, pooling, full connection, etc. Similar to other neural network, CNN is trained by backpropagation. Based on performance, online error backpropagation is used in general. The learning process is an iterative procedure where the weights are updated by a small step in the opposite direction of the steepest gradient. The present invention has found that the use of sonification, i.e. of deriving audio data, in order to convey information, set up on a processed image employs variable tone input, melodic alarms and changes of sound patterns which meaningfully increase the spectrum of diagnosis. Thus, the use of an audio signal corrects the human inability to distinguish between a myriad of two and three dimensional visual cues, which by themselves possess no specificity. On the contrary, pattern signal analysis using classification of data methods and a final integration of data into sound signals by an algorithm using pitch, amplitude, timbre, spatialization and temporal patterns confers a diagnostic advantage. The raw audio signals are then subjected to a second deep learning system (System B) and the final results are audio and/or visual outputs which can be easily assessed in order to recommend the proper medical procedure.

Parameter mapping sonification involves the association of information with auditory parameters for the purpose of data display. Since sound is inherently multidimensional, is particularly well suited for displaying multivariate data. Data exploration is often thought of as the most 'scientific' of sonifications and usually makes use of a type of sonification called parameter based sonification. For example, sonification approaches can be used to interpret and sonify the weighted activations of nodes in a machine learning system (computer aided classification system), including "Raw" weights sonification, Concept Mapping sonification and K-Means sonification.

K-Means is an unsupervised learning algorithm that classifies a given data set into certain number of clusters. The data is preferably gained from the classification systems discussed above, such as the CNN system. The main idea is to define k centroids, one for each cluster. Initially the algorithm preferably places the centroids far away as possible from each other. The next step is to take each point belonging to a given data set and associate it to the nearest centroid. Each point belonging to a given data set is associated to the nearest centroid. When no point is pending, the first step is completed, and an early grouping is done. Again, re-calculate k new centroids as centers of the clusters (resulting from the previous step). Repeat the process until centroids do not move any more. In the successive loops, the k centroids change their location step by step. In the present invention, each image has different features due to the type of skin cancer and such different features are used for classification. Texture is an important aspect of the image including brightness, color, slop and size. Such features are useful from the dataset of the image and can be used in the classification. In the present invention, it has been found that the number of centroids relating to the features of the visual skin image can range from about 8 to about 14 centroids, and more preferably from about 9 to 12. Thus, an image filled with different points of data can be extracted and classified with a subsequent connection to an audio sound, generating various amplitudes, decays and frequencies of the sound. Importantly, the audio sound includes different pitches, loudness, durations, timbres, and other sound attributes to make the malignant lesions sound comparatively more loud, sharp, or urgent than benign lesions. This difference in sound attributes allows an experienced listener to learn to differentiate the sound of different classes of lesions. Notably, using the sound attributes is diagnostically more powerful because audio output based on K-means provides a severity to a data point which utilizes the audio data collection of the brain which is more sensitive as compared to the visual examination. Specifically, using an audio signal based on the K-means data can denote a severe malignant sound and the clinician may excise more margin and provide for a faster follow up based on this message.

The above extraction of data from the Classifier may be a standalone or combined with additional methodologies of sound extraction in order to represent it as sound, as exemplified but not restricted to: Raw weights analysis, i.e. defining an activated point in a processed classifier image as either benign or malign, assigning it a specific weight, and sorting by magnitude the sum of all in order to derive sequential sounds or/and by concept mapping data analysis, i.e. determining an infinite number of parameters, starting with, such as benignness, malignancy, color, as a linear or non-linear function of the distance and polarity of a given image from the benign/malignant/color decision boundary in a complex dimensional space represented by the classifier input, attributing a virtual weight to each, with or without multiplying each parameter by its confidence, average, root mean square, etc. and generating amplitudes, decays, and frequencies of the calculated sum of these activations.

Examples

A convolutional network architecture based on the Inception V2 network[13] was used to classify dermatoscopic images into malignant vs benign (binary classification) and obtain a feature representation for subsequent use in sonification. The network maps an input image into an output feature map that encodes the visual features which were found to be discriminative in classifying lesions.

The System A DL classifier was developed using two publicly available datasets: the International Skin Imaging Collaboration (ISIC) 2017 dataset (2361 images), and the Interactive Atlas of Dermoscopy (IAD) dataset (2000 dermoscopy images and 800 context images). Images in each of these datasets were labeled as either a melanoma or benign lesion based on pathology report. As a consequence, the present DL lesion analysis method was predicting the primary finding from histopathology based solely on the lesion image. Caffe library was employed to train the Inception V2 model parameters using stochastic gradient descent. Data augmentation was used to expand the available training images and provide greater robustness to the variations in lesion presentation that would be expected to occur under field conditions. Training began with a pretrained Inception V2 model which was trained on the ImageNet dataset.[14] Fine tuning of the model was then performed using 800 context images from the IAD dataset. Since context images can provide useful discriminative cues for dermoscopic image analysis[10] multi-task learning was performed, which has been shown to improve the performance of deep network models.[15]

Sonification is the representation of data using non-speech sound.[16] The data here were the weighted activations of all of the 1024 nodes in the penultimate layer of the DL classifier, which were used to generate sounds in several distinct ways. In the sonification design discussed here, a k-means clustering algorithm[17] was used to cluster the 1024 node activations into groups of related observations. Cluster centroids represented by individual pitches and malignant "alert" sounds were mapped onto loudness, timbre, and duration of a sonification, thus an audio signal for each of the centroids of data was derived, providing for an audio output that acoustically differentiated the malignant from benign lesions. The overall effect of this particular sonification approach was to provide global information about the image, and also about how it compares to clusters of known images that are already in the database.

Classification by Sonification: Laboratory Retrospective Study (LARS) Analysis

The sonification algorithms are designed to allow a listener to differentiate the sound of different classes of lesions. This "diagnosis-by-ear" has been successful in human developmental stages, and notably found herein to become a powerful diagnostic tool, akin to the widely used stethoscope. In a clinical setting, however, ambient noise may preclude the use of audio output and require a different quantification methodology. Thus, a method to systematically inspect the sonification output visually for lesion diagnosis was developed herein. An additional machine learning system was developed to diagnose lesions by analyzing Fast Fourier transforms (FFTs) and spectrograms derived from the sonification output (System B). Dermoscopy images (n=482, half benign, and half malignant) from the database of images that the System A classifier was built and used to generate audio files using the k-means sonification algorithm (Supercollider v. 3.8.0).

For each audio file, visual plots were produced (Sigview software, v.3.1.1.0, SignalLab, e.K., Germany) of the audio amplitude, the FFT of the audio, and the spectrogram, as shown in FIG. 1. Three separate versions of this secondary classifier, each with identical CNN architectures, were employed in order to diagnose skin cancer based on the audio, FFT, or spectrogram derived from the sonification. All three classifiers were trained against the ground truth diagnosis in the database, using a single split 80% of the samples (386 randomly selected from the set of 482), and the remaining 20% of the set were held back for validation. All three classifiers normalize the input (zero-mean and divide by standard deviation), and dropout is used for regularization.

Raw audio classifier: Each raw WAV file was a single-channel (mono) audio, produced via the sonification algorithm, with sample rate of 44,100 Hz and a duration of 5 seconds, for a total of 220,500 data points per file. By averaging each 10 consecutive samples, we reduced the input size to 22,050 values. A 1-dimensional convolutional neural network (CNN) was used, with input size 22,050, first convolutional layer with 32 filters of size 1×5; max-pooling layer with size 10; second convolutional layer with 64 filters; max-pooling layer with size 10; a fully connected layer with 128 neurons; and output softmax layer with 2 neurons. This model obtained a validation accuracy of 86.6%.

FFT classifier: The image files were visual depictions of the FFT of the audio files. Two (2) convolutional layers were used, the first with 32 filters, and the second with 64 filters. Each convolutional layer was followed by a max-pooling layer of size 2×2. The two convolutional layers were followed by a fully connected layer with 128 neurons, and output softmax layer with 2 neurons. This model obtained a validation accuracy of 82.3%.

Spectrogram classifier: An identical CNN architecture to the one used for FFT was deployed, with the input files being images of the spectrograms, yielding a validation accuracy of 92.8%.

Clinical Study: The study was approved by the institutional review board of Maccabi Healthcare, Israel (protocol Aq 16842/2017), clinicaltrials.gov Identifier: NCT03362138. An open, prospective, non-interventional clinical trial was conducted in a dermatologic clinic (AD, Tel Aviv, Ill.). Inclusion criteria were: age 18 years and older, a suspected malignant pigmented lesion by dermoscopy resulting in clinical management by referral to biopsy, and patients' consent to participate in the study. Exclusion criteria were a nonintact skin, more than 15 hairs per dermoscopic field, performance of an unsolicited biopsy by surgeon (shave), and lesion location within 1 cm of the eye or mucosae surfaces. A total of 52 consecutive biopsy reports were received, 47 being eligible by inclusion criteria as shown below in Table 1.

TABLE 1

Epidemiologic data and Characteristics of Lesions

| Characteristics | No. 47 |
|---|---|
| Study population | |
| Patients | 47 |
| Lesions | 47 |
| Age, mean, median (range) | 49.6 ± 15.4 (18-87) |
| Sex | |
| Male | 28 |
| Female | 19 |
| Race | |
| Caucasian | 100% |
| Anatomic Site | |
| Face | 11 |
| Trunk | 26 |
| Extremities | 10 |
| Diagnosis | |
| Nevus | 23 |

TABLE 1-continued

Epidemiologic data and Characteristics of Lesions

| Characteristics | No. 47 |
|---|---|
| Skin Cancer | |
| Dysplastic Nevus | 11 |
| Atypical Spitz Nevus | 1 |
| Melanoma | 1 |
| Basal Cell Carcinoma | 4 |
| Squamous Cell Carcinoma | 7 |

Subsequent to a clinical decision to biopsy, patient was referred to surgeon and asked to participate in the study by signing the consent form. A dermoscope (DL4, 3 Gen, Tex., US) attached to a smartphone (iPhone 6) was used through a purpose-built application (HopLabs, Atlanta, Ga., US) for acquiring a dermoscopic image of a lesion. The dermoscopic image of the suspected lesion was transmitted securely to a server (HopLabs, Atlanta, Ga., USA) via a mobile network. Participant ID was transferred as consecutive numbers, without other patient details. Images were processed on the server by the DL algorithm (System A), and the DL outputs were further processed by the sonification algorithm (System B), as previously detailed. A clinical diagnosis, benign or malignant, appears on the smartphone screen within 6-8 sec from acquiring the dermoscopic image, alongside controls to play the sonification audio.

Based on the (LARS) outcomes, clear differences for FFT and spectrogram visual plots were evident for malignant versus benign lesions, as shown in FIG. 1 c-f.

Limited quality of the audio playback by the smartphone loudspeakers in the practical setting resulted in different classifier algorithm outputs for the clinical trial, as compared the LARS setting, preventing use of the original LARS heuristics on clinically-gathered dermoscopies. Thus, the LARS procedure was completed again with the new images from the clinical trial: for each image an audio file was generated using the k-means sonification algorithm; then, for each audio file an FFT and a spectrogram were produced. The area under the curve of the FFT and spectrograms was determined as well in order to quantify differences. For each of these clinical trial images, the frequency range, number of frequency components above 3000 Hz, and the number of saw-tooth wave components was determined. As a result of this systematic evaluation, malignancy was defined for the clinical trial as: (1) a spectrogram with components of greater than 3000 Hz frequency; and/or (2) four or more saw-tooth wave spikes (typically with declining peak heights). These diagnostic heuristics can be used as a human-performed System B classification method, following on the automated System A classifier output.

Success for the new system was detection of malignancies at a Sensitivity of at least 75% for System A and 85% for System B results, as validated by biopsy. (Sensitivity is the percentage of correctly diagnosed malignancies, i.e., true positive/positive diagnoses.) An additional metric of success was a Specificity of at least 33% for Classifier and Sonification, as compared to biopsy. (Specificity is the percentage of correctly identified normal nevi, i.e., true negative/negative diagnoses.)

Statistical Analysis: Baseline and demographic characteristics were summarized by standard descriptive summaries. All statistical tests used in this study were 2-sided and a p value less than 0.05 was considered significant. Receiver Operating Characteristic (ROC) curves were used to compare the DL results to ground truth biopsies. In the ROCs, sensitivity, the true positive rate, was plotted on the y-axis versus [1-Specificity], the false positive rate, on the x-axis. AUC for such a plot has a maximum value of 1.0 and is the standard performance metric in the DL literature.

Results

Laboratory Study Results

Figure 2A:
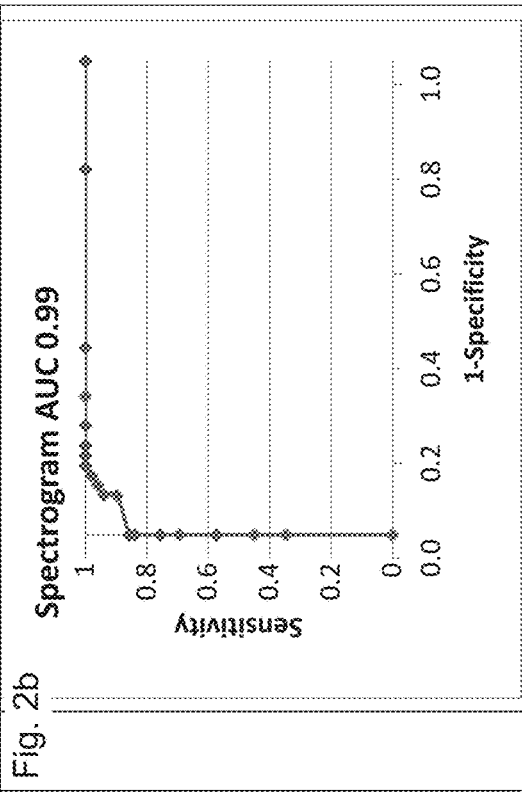
FIGS. 2 a, b, c, d, shows Receiver Operating Characteristic Curves and Area Under the Curve for the Machine Learning System Applied to Sonification Outputs Figures a to c, and DL Classifier Figure d.
Figure 2B:
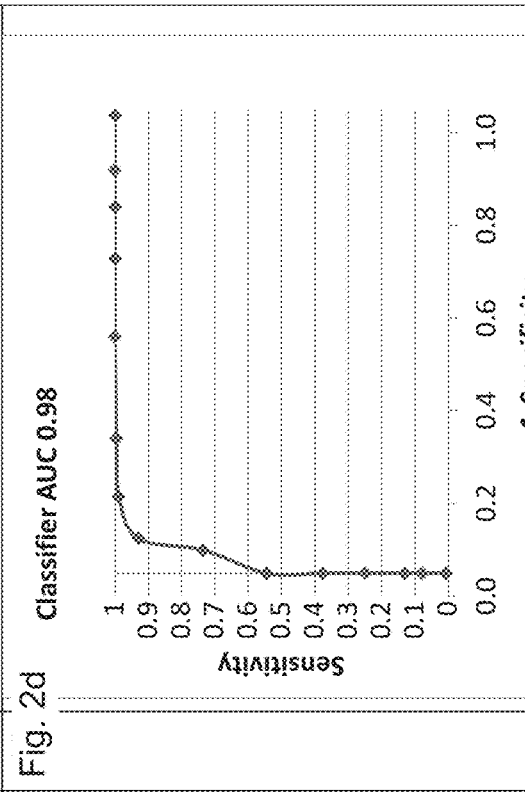
Figure 2C:
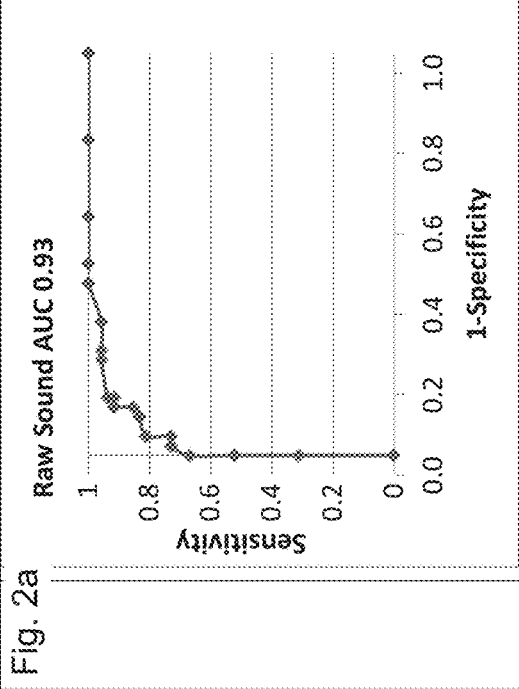
Figure 2D:
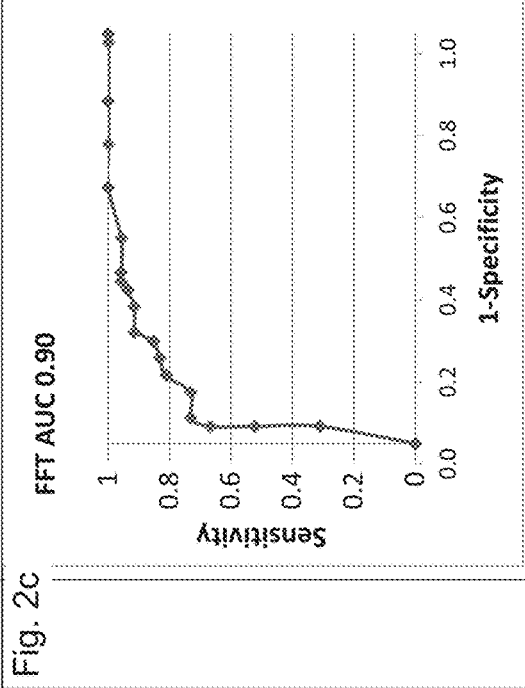

A total of 482 dermoscopies were tested versus ground truth biopsies to determine the diagnostic abilities of raw sound, FFT, spectrograms, and the DL classifier. A machine learning algorithm (previously described) was used to diagnose benign and malignant images, based on raw sound waves (FIGS. 1 a and b.). An AUC of 0.931 (95% CI 0.881-0.981), was achieved shown in FIG. 2a, yielding a remarkable automated diagnostic ability with the raw sound files.

Unlike the raw sound waves, FFT and spectrograms exhibit visually-discernible differences between benign and malignant dermoscopies, which is the result of the intentional sonification design, for example using a saw-tooth wave to sonify images that are classified by System A as malignant.FFT of benign and malignant origins (FIG. 1 c, d) show a >3000 Hz sound frequency, as well as a larger area under the FFT curve. When it comes to the visual spectrograms, malignant biopsies (unlike benign biopsies; FIG. 1 e, f) often also display a characteristic pattern of multiple saw-tooth peaks, declining in amplitude over time.

Applying the second machine-learning algorithm to diagnose malignancy for FFT, spectrograms, and the original DL classifier, resulted in ROC curve AUCs of), 0.90 (95% CI 0.838-0.963), 0.988 (CI 95% 0.973-1.00), and 0.976 (95% CI, 0.965-0.987), respectively, as shown in FIGS. 2 b, c, and d. It was concluded that spectrograms of sonifications based on k-means clustering of DL classifier data (recall, AUC of 0.99) possess the most sensitive means of diagnostic accuracy, which considerably attenuates the false negative results that are typical of current skin cancer diagnosis. Impressively, System B outperformed the very strong performance of System A, which had been built using a larger database of images.

Clinical Study Results: The clinical trial findings provide an independent field test of the resulting classifier. As shown in Table 1, above, a total of 47 biopsies complying with inclusion criteria were analyzed. FIG. 3a depicts the smartphone application, which was used for acquiring images (via an attached dermoscope) and for displaying the System A diagnosis and sonification playback controls.

The LARS dermoscopies used melanomas as a major clinical indicator of malignancy. However, the clinical testing encountered mostly dysplastic nevi (n=12) and only one MM due to a small sample size, which are more of a diagnostic challenge as compared to melanomas. See representative clinical examples of the dysplastic nevi excised which were identified, as shown in FIG. 3 b to f and of those not recognized by System B, as shown in FIG. 3g. The degree of dermoscopic dysplasia of all nevi is borderline, excluding the lesion shown in the in FIG. 3a.

Figure 4I:
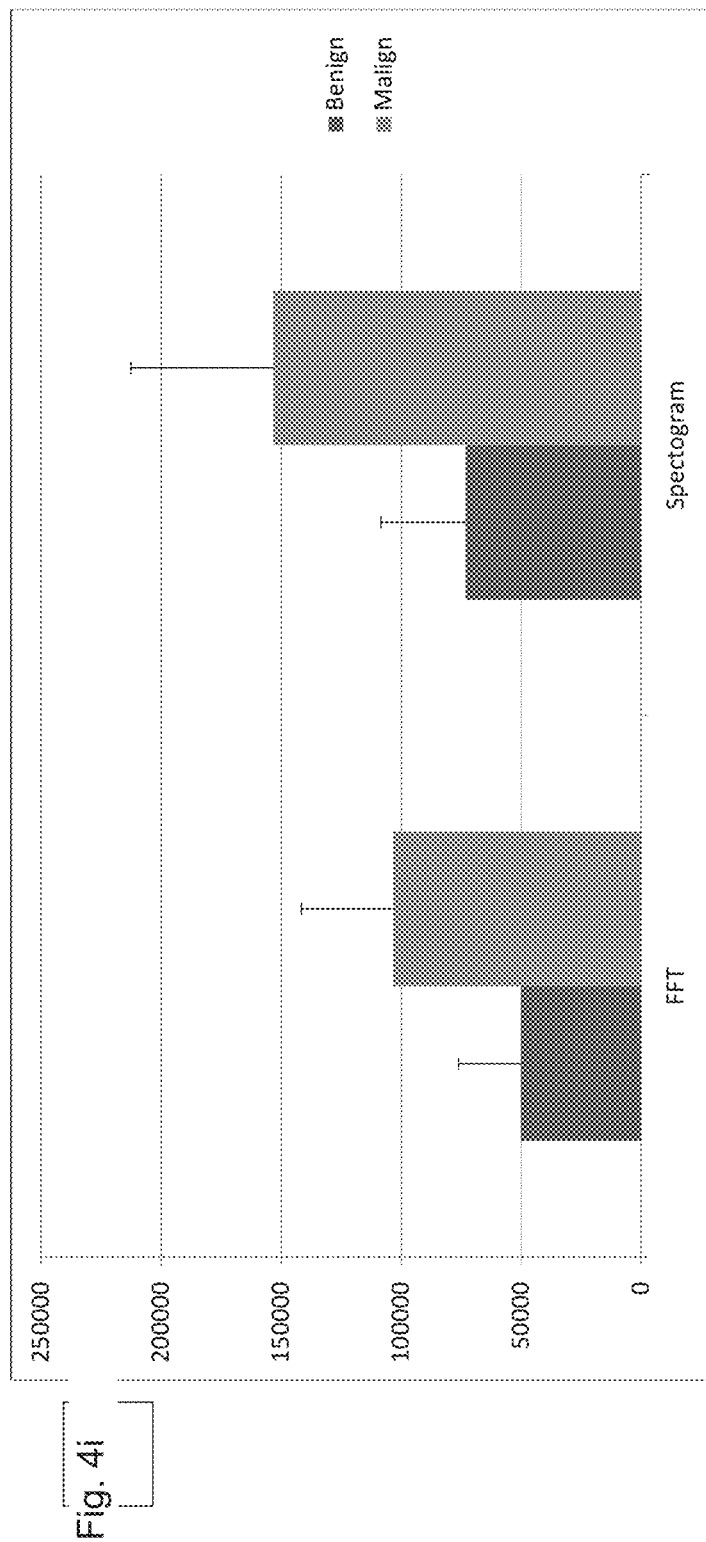
FIGS. 4 a, b, c, d, e, f, g, h, and i shows Clinical Trial Output Examples.

Major markers of malignancy are shared between LARS and clinical images of dermoscopies: benign lesions (FIG. 4 a, b) display a low y-axis span and do not display a >3000 Hz frequency, contrary to malignant dermoscopies (FIG. 4 c, d). Spectrograms of benign (FIG. 4 e, f) and malignant skin lesions (FIG. 4 g, h) conform to the 3000 Hz threshold and show the multiple saw-tooth pattern. The differences are obvious in most, though not all, of the biopsied lesions. FIG. 4i compares benign and malignant lesions and identifies statistically significant differences for FFT ($p<0.001$) and spectrograms ($p<0.0001$). It was concluded that AUC of FFT and spectrograms are objective criteria for identification of malignancy.

FIG. 5 presents a summary of the performance results of System A (DL classifier), System B (sonification and LARS-based heuristic inspection), as well as the combined System A+B in the clinical trial. System A identified 22/23 benign lesions (95.7% specificity). System B correctly identified 22/24 skin cancers (sensitivity of 91.7%). System A seems to excel in specificity and System B excels in sensitivity and grossly replicates the lab simulation tests. The combined use of System A and B as a 2-stage clinical assistance achieves a superhuman accuracy.

The present invention teaches a skin cancer detection system which evaluates two different inputs derived from a dermoscopy image: visual features determined via deep learning (System A); and sonification of deep learning node activations (System B). A laboratory study and a clinical trial confirm the accuracy level of this decision support system. In both LARS and clinical setup, System A is highly specific and System B is highly sensitive; combination of the two systems facilitates clinical diagnosis with improved specificity.

The use of System A accuracy results are consistent with previously published data.[18, 19] A novel contribution of the present invention is the use of sonification with a second machine learning system, which is not commonly used as a diagnostic tool.[20] The LARS achieves an AUC of 0.99 with the spectrograms in System B, as compared to 0.96 for the DL classifier in System A. In the clinical trial, sensitivity is greatly improved from System A (54%) to System B (92%). System B achieved its primary outcomes of specificity and sensitivity. System A achieved an unprecedented and surprising specificity of 96%, but not its primary single diagnostic specificity outcome. Combining both Systems seems to endow any clinician with a formidable assistance tool.

Dysplastic nevi are considered to be of malignant potential, due to their risk for developing into melanoma,[21] and especially in light of current publications casting doubt on pathologists' ability to discern moderate from severe dysplastic nevi.[22] The present system was assessed under harsh field testing, performing diagnosis of minimal dysplasia—a fine-features dermoscopy challenge—as part of the criteria of sensitivity. These results further emphasize the high sensitivity of System B.

As part of the initial line of thought in this project, the clinician was expected to evaluate nevi by supplementing System A by listening to the sonification output. Due to the inconvenience of sound perception in the clinic, and in order to increase accuracy, it was decided to develop a second machine learning algorithm for analyzing the sonification output (transformed into spectrograms), rendering clinician diagnosis-by-ear as optional. Two heuristic criteria seem to be critical to malignancy recognition of the spectrograms, both in the LARS and clinical trial: a frequency of >3000 Hz and four or more spikes of audio intensity. An accurate operative telemedicine prototype as a tool for cloud-directed diagnosis is a field which might be further improved, rendering this system as a candidate for use in the detection of unimaged skin cancer.

It is known that pathology reports of melanoma diagnosis are disputable in about 15% of reports.[21] However, the present system is sensitive enough to identify fine details of dysplastic nevi, its sensitivity will increase further with melanoma detection to a degree comparable with LARS, which was trained mostly with melanomas.

The present invention provides a new diagnostic method for cancerous skin lesions detection and achieved a high accuracy in both a laboratory study and a clinical trial. Algorithms used herein employ dual deep learning classifiers, and sonification results of the output of the first classifier was further analyzed using a second deep learning system that provides not only an audible signal but visual data.

REFERENCES

The references cited herein are incorporated by reference herein for all purposes.
1. American Cancer Society. Cancer facts & figures 2016. Atlanta, American Cancer Society 2018. http://www.cancer.org/acs/groups/content/@research/documents/document/acspc-047079.pdf. https://www.cancer.org/research/cancer-facts-statistics/all-cancer-facts-figures/cancer-facts-figures-2018.html
2. Carrera C, Marchetti M A, Dusza S W et al. Validity and Reliability of Dermoscopic Criteria Used to Differentiate Nevi From Melanoma: A Web-Based International Dermoscopy Society Study. *JAMA Dermatol.* 2016 Jul. 1; 152(7):798-806.
3. Tschandl P, Hofmann L, Fink C et al. Melanomas vs. nevi in high-risk patients under long-term monitoring with digital dermatoscopy: do melanomas and nevi already differ at baseline?*J Eur Acad Dermatol Venereol.* 2017 June; 31(6):972-977.
4. Matsumoto M, Secrest A, Anderson A et al. Estimating the cost of skin cancer detection by dermatology providers in a large health care system. *J Am Acad Dermatol.* 2018 April; 78(4):701-709.el.
5. Waldmann A, Nolte S, Geller A C, et al. Frequency of excisions and yields of malignant skin tumors in a population-based screening intervention of 360,288 whole-body examinations. *Arch Dermatol.* 2012; 148(8):903-910.
6. Winkelmann R R, Farberg A S, Glazer A M et al Integrating Skin Cancer-Related Technologies into Clinical Practice. *Dermatol Clin.* 2017 October; 35(4):565-576.
7. Brunssen Al, Waldmann A, Eisemann N et al. Impact of skin cancer screening and secondary prevention campaigns on skin cancer incidence and mortality: A systematic review. *J Am Acad Dermatol.* 2017 January; 76(1): 129-139.
8. Gulshan V, Peng L, Coram M. et al. Development and Validation of a Deep Learning Algorithm for Detection of Diabetic Retinopathy in Retinal Fundus Photographs. *JAMA.* 2016 Dec. 13; 316(22):2402-2410.
9. Ehteshami Bejnordi B, Veta M, Johannes van Diest P et al. Diagnostic Assessment of Deep Learning Algorithms for Detection of Lymph Node Metastases in Women With Breast Cancer. *JAMA.* 2017 Dec. 12; 318(22):2199-2210.
10. Esteva A, Kuprel B, Novoa R A et al. Dermatologist-level classification of skin cancer with deep neural networks. *Nature.* 2017 Feb. 2; 542(7639):115-118.
11. Han S S, Kim M S, Lim W et al. Classification of the Clinical Images for Benign and Malignant Cutaneous Tumors Using a Deep Learning Algorithm. *J Invest Dermatol.* 2018 Feb. 8. pii: S0022-202X (18)30111-8.
12. Dubus G, Bresin. A systematic review of mapping strategies for the sonification of physical quantities. *RPLoS One.* 2013 Dec. 17; 8(12).
13. Ioffe, S., & Szegedy, C. (2015). Batch Normalization: Accelerating Deep Network Training by Reducing Internal Covariate Shift. In Proceedings of the 32nd International Conference on Machine Learning (ICML) (Vol. 37). Lille, France
14. Russakovsky, O., Deng, J., Su, H., et al. (2015). ImageNet Large Scale Visual Recognition Challenge. *International Journal of Computer Vision,* 115(3), 211-252
15. Yu L, Chen H, Dou Q, Qin J, Heng P A. Automated Melanoma Recognition in Dermoscopy Images via Very Deep Residual Networks. *IEEE Trans Med Imaging.* 2017 April; 36(4): 994-1004.
16. Li X, Zhao L, Wei L, Yang M H et al. Deep Saliency: Multi-Task Deep Neural Network Model for Salient Object Detection. *IEEE Trans Image Process.* 2016 August; 25(8):3919-30.
17. Walker, B. N., & Nees, M. A. (2011). Theory of Sonification. In T. Hermann, A. Hunt, & J. Neuhoff (Eds.), *The Sonification Handbook* (pp. 9-39). Berlin, Germany: Logos Publishing House. ISBN 978-3-8325-2819-5.
18. Shraddha S and Naganna S. A Review on K-means data Clustering approach. *International Journal of Information & Computation Technology.* ISSN 0974-2239 Volume 4, Number 17 (2014), pp. 1847-1860
19. Han S S, Kim M S, Lim W et al. Classification of the Clinical Images for Benign and Malignant Cutaneous Tumors Using a Deep Learning Algorithm. *J Invest Dermatol.* 2018 Feb. 8. pii: S0022-202X (18)30111-8
20. Poveda J, O'Sullivan M, Popovici E et al. Portable neonatal EEG monitoring and sonification on an Android device. *Conf Proc IEEE Eng Med Biol Soc.* 2017 July; 2017:2018-2021.
21. Melamed R D, Aydin I T, Rajan G S et al. Genomic Characterization of Dysplastic Nevi Unveils Implications for Diagnosis of Melanoma. *J Invest Dermatol.* 2017; 137(4):905.
22. Elmore J G, Barnhill R L, Elder D E et al. Pathologists' diagnosis of invasive melanoma and melanocytic proliferations: observer accuracy and reproducibility study. *BMJ.* 2017 Jun. 28; 357: j2813.
23. Gendreau J L, Gemelas J, Wang M, Capu. Unimaged Melanomas in Store-and-Forward Teledermatology. *Telemed J E Health.* 2017 June; 23(6):517-520.
23. King A J. Multisensory Integration: Strategies for Synchronization. *Current Biology,* Volume 15, Issue 9, 10 May 2005, Pages R339-R341.
24. Gaizauskas, B R. The Harmony of the Spheres. *Journal of the Royal Astronomical Society of Canada,* Vol. 68, p. 146.
25. Neuhoff J G, Kramer G, Wayand J. Pitch and loudness interact in auditory displays: can the data get lost in the map. *J Exp Psychol Appl.* 2002 March; 8(1): 17-25.
26. Han Y C, Han B. Pattern Sonification as a New Timbral Expression. *Leonardo Music Journal,* Volume 24, 2014, pp. 41-43.
27. Scholz D S, Wu L, Pirzer J, et al Sonification as a possible stroke rehabilitation strategy. *Front Neurosci.* 2014 Oct. 20; 8: 332.
28. Ahmad A, Adie S G, Wang M, Boppart S A. Sonification of optical coherence tomography data and images. *Opt Express.* 2010 May 10; 18(10): 9934-44.
29. Dubus G and Bresin R. A Systematic Review of Mapping Strategies for the Sonification of Physical Quantities. *PLos One,* 2013; 8(12): e82491.
30. AHRQ Publication No. 11-EHC085-EF, Noninvasive Diagnostic Techniques for the Detection of Skin Cancers, September 2011.

That which is claimed is:

1. A method of diagnosing skin cancer in a subject, the method comprising:
   obtaining an image of a tissue sample suspected of being cancerous;
   extracting a plurality of features from the image, wherein the features include texture, brightness, shape, color, size, and/or quality of tissue;
   classifying the plurality of features using a first computer-aided classifier;
   introducing the classified plurality of features into a computer-aided clustering algorithm to obtain clusters of data relating to each tissue type in the image;
   converting, by sonification techniques, the clusters of data to audio signals; and
   analyzing the audio signals using a second computer-aided classifier, wherein an audio output from the second computer-aided classifier acoustically differentiates malignant from benign lesions,
   wherein the subject has skin cancer if the audio output indicates the lesion is malignant.

2. The method of claim 1, wherein the image is obtained using photography, dermoscopy, molecular scattering, thermography, multiphoton fluorescence microscopy, multiphoton excitation microscopy, optical coherence tomography, or confocal scanning laser microscopy.

3. The method of claim 1, wherein the plurality of features of the image are extracted and grouped into a plurality of segments for classifying by the first computer-aided classifier.

4. The method of claim 1, wherein the first computer-aided classifier is a deep learning classifier.

5. The method of claim 4, wherein the deep learning classifier comprises a convolution Neural Network.

6. The method of claim 1, wherein the clustering algorithm is an unsupervised, supervised, semisupervised, or reinforcement learning clustering algorithm.

7. The method of claim 1, wherein for each image an audio file is generated using k-means sonification algorithms.

8. The method of claim 1, wherein the audio signals are selected from the group consisting of different pitch, loudness, timbre, duration, spatialization and temporal patterns of each visual feature.

9. The method of claim 1, wherein the audio output is communicated by headphones, speaker, smartphone, computer, tablet, mobile device, watch, Bluetooth device or a device that provides a tactile or vibration signal.

10. The method of claim 1, wherein the second computer-aided classifier is a deep learning classifier.

11. The method of claim 10, wherein deep learning classifier comprises a Convolution Neural Network.

12. The method of claim 1, wherein the sonification technique comprises a parameter mapping sonification method wherein a classification method and/or a clustering algorithm is used to isolate clusters of data related to each tissue type and then assign a unique audio signal to each tissue type.

13. The method of claim 1, wherein the tissue sample suspected of being cancerous comprises a lesion selected from the group consisting of atypical melanocytic hyperplasia, atypical mole, dysplastic mole, melanoma, cancerous skin diseases, actinic keratosis, basal cell carcinoma, and squamous cell carcinoma.

14. The method of claim 1, wherein the audio signal comprises different output sounds differentiated by at least one of frequency, duration, magnitude, spectrum, and spatial orientation.

15. The method of claim 14, wherein malignant lesions sound comparatively more loud, sharp, or urgent than benign lesions.

16. The method of claim 1, wherein the clustering algorithm can be visualized by grouping features by K-means, hierarchical clustering or feature agglomeration.

17. The method of claim 1, wherein a visual output can be obtained from the first computer-aided classifier, wherein the visual output can be used to identify if the lesion is benign or malignant.

18. The method of claim 7, wherein for each audio file, the method further comprises producing a Fast Fourier Transform (FFTs) and/or a spectrogram, which exhibit visually-discernible differences between benign and malignant lesions.

* * * * *